United States Patent [19]

Dawes et al.

[11] 4,055,572

[45] Oct. 25, 1977

[54] PROCESS FOR THE PRODUCTION OF 3-HYDROXY-1,2,4-TRIAZOLE DERIVATIVES

[75] Inventor: Dag Dawes, Voyenenga, Norway; Rudolph C. Thummel, Courgenay, Switzerland

[73] Assignee: Ciba-Geigy Corporation, Ardsley, N.Y.

[21] Appl. No.: 707,148

[22] Filed: July 20, 1976

[30] Foreign Application Priority Data

Aug. 6, 1975 Switzerland ............... 10241/75
June 25, 1976 Switzerland ............... 8152/76

[51] Int. Cl.$^2$ ........................... C07D 249/12
[52] U.S. Cl. ............... 260/308 R; 260/308 C; 260/464; 260/465.5 R; 260/583 B; 260/563 R; 260/563 C
[58] Field of Search ............... 260/308 R, 308 C

[56] References Cited

U.S. PATENT DOCUMENTS

| 3,133,933 | 5/1964 | Ruschig et al. | 260/308 |
| 3,184,470 | 5/1965 | Ruschig et al. | 260/308 |
| 3,666,771 | 5/1972 | Hoefle et al. | 260/308 |

FOREIGN PATENT DOCUMENTS 94,570 10/1962 Denmark

OTHER PUBLICATIONS

Patai–"The Chemistry of the Cyano Group", (1970), Interscience Publishers–pp. 264, 265, 267.

Primary Examiner—Raymond V. Rush
Attorney, Agent, or Firm—Harry Falber

[57] ABSTRACT

A process for the production of 3-hydroxy-1,2,4-triazole derivatives of formula I (I)

-continued $$R_1-N-N$$
$$R_2-X-C\phantom{xx}C-OH$$
$$\phantom{xxxx}N$$

wherein
 $R_1$ and $R_2$ each represent a straight-chain or branched-chain alkyl group having 1 to 6 carbon atoms, or a cycloalkyl group having 3 to 6 carbon atoms, and
 X represents oxygen or sulphur,
which process comprises adding to a 1-alkyl-1-cyanohydrazine of formula II $$R_1-N-NH_2$$
$$\phantom{xx}|$$
$$\phantom{xx}C\equiv N$$

(II)

wherein $R_1$ has the meaning given under formula I, a compound of formula III $$R_2-XH$$

(III)

wherein $R_2$ and X have the meanings given under formula I;
and subsequently cyclising the addition product by reaction with a compound of formula IV $$\phantom{xxx}O$$
$$\phantom{xxx}\|$$
$$R_4-C-R_3$$

(IV)

wherein $R_3$ and $R_4$ independently of one another represent chlorine or an alkoxy group having 1 to 4 carbon atoms.

The 3-hydroxy-1,2,4-triazole derivatives are valuable intermediates for producing phosphoric acid esters which can be used as pesticidal agents, particularly as insecticides and nematicides.

6 Claims, No Drawings

PROCESS FOR THE PRODUCTION OF 3-HYDROXY-1,2,4-TRIAZOLE DERIVATIVES

The present invention relates to a process for the production of 3-hydroxy-1,2,4-triazole derivatives of formula I

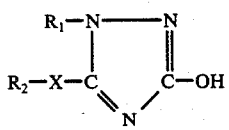
(I)

wherein
$R_1$ and $R_2$ each represent a straight-chain or branched-chain alkyl group having 1 to 6 carbon atoms, or a cycloalkyl group having 3 to 6 carbon atoms, and
X represents oxygen or sulphur.

The 3-hydroxy-1,2,4-triazole derivatives of formula I are valuable intermediates for producing phosphoric acid esters which can be used as pesticidal agents, particularly as insecticides and nematicides. Such phosphoric acid esters and their use are described in the U.S. Pat. No. 3,867,398. The product of 3-hydroxy-1,2,4-triazole derivatives of formula I by the reaction of corresponding 1-alkyl-3-hydroxy-5-chloro-1,2,4triazoles with alkylmercaptides or with alcoholates is known (see U.S. Pat. No. 3,867,398). The 1-alkyl-3-hydroxy-5-chloro-1,2,4-triazoles are for their part obtained by reacting a 1-alkylsemicarbazide with formic acid to the corresponding 1-alkyl-3-hydroxy-1,2,4-triazole (Ber. dtsch. Chem. Ges. 26, 2613, (1893)), and subsequently chlorinating this in the 5-position (see U.S. Pat. No. 3,867,396). This known process is unsatisfactory not only because it requires a large number of reaction steps but also because it falls short with respect to the attained yields.

It has now been found that the 3-hydroxy-1,3,4-triazole derivatives of formula I can be produced in a simple manner by adding to a 1-alkyl-1-cyanohydrazine of formula II

(II), wherein $R_1$ has the meaning given under formula I, a compound of formula III $$R_2 - XH \qquad (III)$$

wherein $R_2$ and X have the meanings given under formula I;
and subsequently cyclising the addition product by reaction with a compound of formula IV

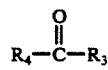
(IV)

wherein $R_3$ and $R_4$ independently of one another represent chlorine or an alkoxy group having 1 to 4 carbon atoms.

The process of the invention is advantageously performed in an inert solvent. Suitable inert solvents are, in particular, chlorinated hydrocarbons such as methylene chloride, chloroform, carbon tetrachloride and tetrachloroethane, ethers such as lower dialkyl ethers, tetrahydrofuran and dioxane, or alcohols derived from the radical $R_2$. The reaction of a mercaptan of formula III can also be performed in water or in a two-phase system composed of water and an organic solvent immiscible with water, whereby suitable solvents immiscible with water are, in particular, the chlorinated hydrocarbons already mentioned.

The reaction of a 1-alkyl-1-cyanohydrazine of formula II with a compound of formula III is preferably carried out in the presence of bases, e.g. alkali metal hydroxide such as sodium hydroxide and potassium hydroxide, or alcoholates such as sodium alcoholates and potassium alcoholates. The reaction of a 1-alkyl-1-cyanohydrazine of formula II with a mercaptan of formula III can also be performed in the presence of acids, e.g. hydrochloric acid.

The process of the invention is preferably performed either by placing into the reaction vessel a solution of a compound of formula III with one of the aforementioned bases, and then adding dropwise to this solution 1-alkyl-1-cyanohydrazine at a temperature of between 0° and 250° C, preferably between 15° and 120° C; or placing the 1-alkyl-1-cyanohydrazine into the reaction vessel, and subsequently adding a solution of a compound of formula III with one of the aforementioned bases at a temperature of between 0° and 250° C, preferably between 15° and 120° C. The resulting 0-alkylisosemicarbazides or S-alkylisothiosemicarbazides of formula V

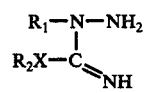
(V), wherein $R_1$, $R_2$ and X have the meanings given under formula I, are not isolated but are cyclised immediately by reaction with phosgene or with a lower chloroformic acid ester or with a lower carbonic acid ester. Cyclisation is performed at a temperature of between 20° and 100° C, whereby the reactants are firstly brought together at a temperature of between about 20° and 50° C, and the reaction is completed by subsequent heating. It is advantageous to perform cyclisation in the presence of a base, with suitable bases being, e.g., pyridine, triethylamine or alkyli metal hydroxides, alkali metal carbonates and alkali metal bicarbonates.

The 3-hydroxy-1,2,4-triazole derivatives of formula I are isolated from aqueous reaction mixtures after acidifying, either by crystallisation or by extraction. From reaction mixtures, which contain one of the aforementioned organic solvents, the final products are either precipitated by the addition of glacial acetic acid or obtained, after removal of the solvent by evaporation, by crystallisation or extraction of the residue. Suitable solvents both for the extraction from aqueous reaction mixtures and for the extraction of the residue obtained after removal of the alcohol by evaporation are, in particular, chlorinated hydrocarbons such as methylene chloride, chloroform, carbon tetrachloride and tetrachloroethane.

The 1-alkyl-1-cyanohydrazines of formula II which are used as starting material can be obtained by reaction of a corresponding alkylhydrazine with cyanogen chloride in the presence of an acid-binding agent. The reaction is advantageously performed in a two-phase reaction medium consisting of water and an organic solvent immiscible with water, with suitable solvents being, in particular, lower halogenated hydrocarbons, especially methylene chloride. The reaction is carried out at a temperature of between 0° and 30° C. Suitable acid-binding agents are, in particular, alkali metal hydroxides, alkali metal carbonates and especially alkali metal hydrogen carbonates. The reaction is performed, for example, by adding to a solution of a corresponding alkylhydrazine in methylene chloride an aqueous solution of the acid-binding agent, and then adding dropwise or feeding in, with stirring, cyanogen chloride. After completed reaction, the formed 1-alkyl-1-cyanohydrazine can be isolated by separation of the aqueous phase and removal of the organic solvent by evaporation in vacuo.

It is possible by means of the process of the invention to produce the 3-hydroxy-1,3,4-triazole derivatives of formula I in a particularly simple manner and in very good yields.

The process of the invention is further illustrated by the following Examples.

EXAMPLE 1

19.8 g (0.2 mole) of 1-isopropyl-1-cyanohydrazine is added dropwise to a solution of 16.0 g (0.4 mole) of sodium hydroxide and 12.4 g (0.2 mole) of ethyl mercaptan in 75 ml of water. Into the resulting white emulsion there is then introduced 19.8 g (0.2 mole) of phosgene at room temperature, and an exothermic reaction occurs. The reaction mixture cooled to room temperature, from which has separated out a white-yellow precipitate, is extracted with methylene chloride and the extract is dried with sodium sulphate. After removal of the methylene chloride by evaporation in vacuo, the crude product is purified by dissolving it in 50 ml of methanol, treating the solution with animal charcoal and crystallising the resulting product at −50° C. There is obtained 1-isopropyl-3-hydroxy-5-ethylthio-1,2,4-triazole, m.p. 109°–114° C.

EXAMPLE 2

19.8 g (0.2 mole) of 1-isopropyl-1-cyanohydrazine is added dropwise to a solution of 8.0 g (0.2 mole) of sodium hydroxide and 12.4 g (0.2 mole) of ethyl mercaptan in 150 ml of water, whereby a slightly exothermic reaction occurs. An addition is then made dropwise, at 20° to 25° C, of 21.7 g (0.2 mole) of chloroformic acid ethyl ester, and the reaction mixture is subsequently refluxed for 1½ hours. On cooling of the reaction mixture to room temperature, there is precipitated an oil. The reaction mixture is extracted twice with 150 ml of chloroform each time; the extract is dried over sodium sulphate and the solvent is evaporated off in vacuo. The white crystalline residue is dissolved in 75 ml of methanol, the solution is treated with animal charcoal and crystallisation is effected at −70° C. There is obtained in this manner 1-isopropyl-3-hydroxy-5-ethylthio-1,2,4-triazole, m.p. 109°–113° C.

EXAMPLE 3

99.0 g (1 mole) of 1-isopropyl-1-cyanohydrazine is added dropwise at an intial temperature of 60° C to a solution of 0.5 g of sodium in 32.1 g (1 mole) of methanol, the manner of addition being such that, as a result of the exothermic reaction, the temperature of the reaction mixture at the completion of the dropwise addition is 110° C. Stirring is maintained at this temperature for a further 30 minutes, and the reaction mixture is subsequently distilled under reduced pressure. There is thus obtained 0-methyl-2-isopropylisosemicarbazide, b.p. 93° C at 12 mm Hg and m.p. 45°–46° C, in the pure form.

EXAMPLE 4

99.0 g (1.0 mole) of 1-isopropyl-1-cyanohydrazine is added dropwise, initialy at boiling temperature, to a solution of 0.5 g of sodium metal in 32.1 g (1.0 mole) of methanol, whereupon an exothermic reaction occurs and the temperature of the reaction mixture rises towards the end of the reaction to 110° C. The reaction mixture crystallises on cooling. The o-methyl-2-isopropyl-isosemicarbazide thus obtained is then dissolved, without further isolation, in a mixture of 202 g (2.0 moles) of triethylamine and 500 ml of ether. This solution is added dropwise at 0° C to a prepared solution of 99.0 g (1.0 mole) of phosgene in 500 ml of ether. The reaction mixture is subsequently refluxed for a further 1 hour, and the formed triethylamine hydrochloride is filtered off. After removal of the ether by evaporation, the oily residue crystallises on cooling in an ice bath. Recrystallisation from ether yields 1-isoproyl-3-hydroxy-5-methoxy-1,2,4-triazole, m.p. 104°–105° C.

I claim:
1. Process for the production of 3-hydroxy-1,2,4-triazole derivatives of formula I

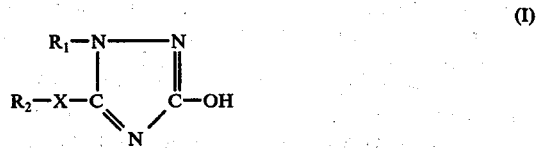

wherein
$R_1$ and $R_2$ each represent a straight-chain or branched-chain alkyl group having 1 to 6 carbon atoms, or a cycloalkyl group having 3 to 6 carbon atoms, and
X represents oxygen or sulphur,
which process comprises reacting a 1-alkyl-1-cyanohydrazine of formula II

wherein $R_1$ has the meaning given under formula I, in an inert solvent in the presence of a base at a temperature of 0° – 250° C. with a compound of formula III

wherein $R_2$ and X have the meanings given under formula I; and subsequently cyclising the reaction product at a temperature of 20° – 100° C. in the presence of a base by reaction with a compound of formula IV

wherein $R_3$ and $R_4$ independently of one another represent chlorine or an alkoxy group having 1 to 4 carbon atoms.

2. Process according to claim 1, wherein there is used a solvent from the group comprising chlorinated hydrocarbons, ethers, and alcohols derived from the radical $R_2$.

3. Process according to claim 1, wherein the reaction of a mercaptan of formula III is performed in water or in a two-phase system composed of water and an organic solvent immiscible with water.

4. Process according to claim 3, wherein the reaction of a mercaptan of formula III is performed in a two-phase system composed of water and a chlorinated hydrocarbon.

5. Process according to claim 1, wherein the reaction of a compound of formula III with a 1-alkyl-1-cyanohydrazine of formula II is performed in the presence of alkali metal hydroxide or alkali metal alcoholate.

6. Process according to claim 1, wherein the addition of a compound of formula III to the 1-alkyl-1-cyanohydrazine of formula II is performed at a temperature of between 20° and 120° C, and the subsequent cyclisation of the resulting addition product with a compound of formula IV at a temperature of between 20° and 100° C in the presence of pyridine, triethylamine, alkali metal hydroxide, alkali metal carbonate or alkali metal bicarbonate.

* * * * *